United States Patent
Kruecker et al.

(10) Patent No.: US 11,051,902 B2
(45) Date of Patent: Jul. 6, 2021

(54) SYSTEM AND METHOD FOR PLANNING AND PERFORMING A REPEAT INTERVENTIONAL PROCEDURE

(71) Applicants: Jochen Kruecker, Andover, MA (US); Pingkun Yan, Gaithersburg, MD (US); Amir Mohammad Tahmasebi Maraghoosh, Arlington, MA (US); Peter A Pinto, Bethesda, MD (US); Bradford Johns Wood, Potomac, MD (US)

(72) Inventors: Jochen Kruecker, Andover, MA (US); Pingkun Yan, Gaithersburg, MD (US); Amir Mohammad Tahmasebi Maraghoosh, Arlington, MA (US); Peter A Pinto, Bethesda, MD (US); Bradford Johns Wood, Potomac, MD (US)

(73) Assignees: KONINKLIJKE PHILIPS N.V., Eindhoven (NL); THE UNITED STATES OF AMERICA, as represented by the SECRETARY, DEPT OF HEALTH AND HUMAN SERVICES, Bethesda, MA (US)

(*) Notice: Subject to any disclaimer, the term of this patent is extended or adjusted under 35 U.S.C. 154(b) by 178 days.

(21) Appl. No.: 15/754,602

(22) PCT Filed: Aug. 10, 2016

(86) PCT No.: PCT/IB2016/054805
§ 371 (c)(1),
(2) Date: Feb. 23, 2018

(87) PCT Pub. No.: WO2017/042650
PCT Pub. Date: Mar. 16, 2017

(65) Prior Publication Data
US 2020/0222119 A1    Jul. 16, 2020

Related U.S. Application Data
(60) Provisional application No. 62/215,775, filed on Sep. 9, 2015.

(51) Int. Cl.
*A61B 5/05*       (2021.01)
*A61B 90/00*      (2016.01)
(Continued)

(52) U.S. Cl.
CPC .............. *A61B 90/36* (2016.02); *A61B 8/085* (2013.01); *A61B 8/0841* (2013.01); *A61B 8/463* (2013.01);
(Continued)

(58) Field of Classification Search
CPC ........ A61B 34/10; A61B 90/36; A61B 8/0841
See application file for complete search history.

(56) References Cited

U.S. PATENT DOCUMENTS

2008/0161687 A1    7/2008  Suri et al.
2009/0118640 A1    5/2009  Miller et al.
(Continued)

FOREIGN PATENT DOCUMENTS

| WO | 2006089426 A1 | 8/2006 |
| WO | 2010140075 A2 | 12/2010 |
| WO | 2015003895 A1 | 1/2015 |

*Primary Examiner* — Joel F Brutus
(74) *Attorney, Agent, or Firm* — Sherry Austin

(57) ABSTRACT

A system for planning and performing a repeat interventional procedure includes a registration device (116) and an image generation device (120) which map current targets in a reference image (104) for a first interventional procedure to at least one guidance image (112) acquired from a different imaging modality. Biopsy locations are recorded to (Continued)

the guidance images during the first interventional procedure and the biopsy locations are mapped to the reference image to provide a planning image for use in a subsequent interventional procedure on the patient. In a subsequent interventional procedure, the prior planning image (124) may be registered to a current reference image (126) and the prior biopsy locations and prior and current targets are mapped to a guidance image acquired from a different imaging modality. Biopsy locations are then mapped to the guidance image (115) and mapped back to the current reference image.

19 Claims, 4 Drawing Sheets

(51) Int. Cl.
| | |
|---|---|
| *A61B 34/10* | (2016.01) |
| *G16H 10/40* | (2018.01) |
| *G16H 30/20* | (2018.01) |
| *G16H 50/30* | (2018.01) |
| *G16H 50/20* | (2018.01) |
| *G16H 30/40* | (2018.01) |
| *A61B 8/08* | (2006.01) |
| *A61B 8/00* | (2006.01) |
| *G06T 7/00* | (2017.01) |
| *G06T 11/00* | (2006.01) |
| *G16H 20/40* | (2018.01) |
| *G16H 40/63* | (2018.01) |
| *G16H 70/20* | (2018.01) |
| *A61B 10/02* | (2006.01) |

(52) U.S. Cl.
CPC ............ *A61B 8/5261* (2013.01); *A61B 34/10* (2016.02); *G06T 7/0014* (2013.01); *G06T 11/003* (2013.01); *G16H 10/40* (2018.01); *G16H 20/40* (2018.01); *G16H 30/20* (2018.01); *G16H 30/40* (2018.01); *G16H 40/63* (2018.01); *G16H 50/20* (2018.01); *G16H 50/30* (2018.01); *G16H 70/20* (2018.01); *A61B 10/0241* (2013.01); *A61B 2034/107* (2016.02); *A61B 2090/374* (2016.02); *G06T 2207/10088* (2013.01); *G06T 2207/10132* (2013.01); *G06T 2207/30081* (2013.01); *G06T 2207/30204* (2013.01)

(56) References Cited

U.S. PATENT DOCUMENTS

2010/0286517 A1    11/2010  Kamen et al.
2014/0073907 A1*   3/2014  Kumar ............... A61B 10/0241
                                                                               600/414

\* cited by examiner

SYSTEM AND METHOD FOR PLANNING AND PERFORMING A REPEAT INTERVENTIONAL PROCEDURE

CROSS-REFERENCE TO PRIOR APPLICATIONS

This application is the U.S. National Phase application under 35 U.S.C. § 371 of International Application Serial No. PCT/IB2016/054805, filed on Aug. 10, 2016, which claims the benefit of U.S. Patent Application No. 62/215,775, filed on Sep. 9, 2015. This application is hereby incorporated by reference herein.

This invention was made with Government support under Cooperative Research and Development Agreement no. 01864 awarded by the United States Government Public Health Service. The Government has certain rights in this invention.

BACKGROUND

Technical Field

This disclosure relates to systems and methods for planning and performing interventional procedures and, in particular, systems and methods for planning and performing repeat interventional procedures.

Description of the Related Art

Biopsies are commonly used to detect cancerous tissues in many areas of the body, such as the prostate. However, ultrasound does not accurately visualize prostate cancer lesions. Furthermore, ultrasound-visualized anatomical landmarks present in the prostate to locate and track specific tissue regions are sometimes less reliable than needed. Therefore, prostate tissue is typically sampled randomly and independently during each repeat biopsy procedure.

Patients that are suspected of having prostate cancer may undergo several repeat biopsy procedures without a positive diagnosis of cancer because the prostate is sampled randomly each time, without image-based lesion targeting. This may lead to repeated sampling of the same benign regions of the gland, while potentially missing cancerous regions outside the sampled areas. Abnormal findings obtained during one procedure are often unable to be tracked over time with repeat sampling in the same location. Furthermore, deliberate and efficient sampling of previously missed locations is not possible.

Recent image guidance systems permit registration of magnetic resonance imaging ("MRI") scans of the prostate with ultrasound imaging for planning and guiding prostate biopsies. This allows precise targeting of lesions identified in the MRI, without the need for an MRI in-gantry procedure. However, a substantial number of prostate cancer lesions and pre-cancerous abnormalities are not visualized on MRI. These abnormalities may be detected incidentally on "systematic" biopsies that are also spatially tracked and recorded on the known systems. However, any biopsy findings recorded in one MRI scan are not able to be transferred efficiently to a subsequent MRI scan and used for planning or targeting purposes.

SUMMARY

In accordance with the present principles, a system for planning and performing a repeat interventional procedure includes a storage device configured to store a reference image of a region of a subject having a reference image coordinate space. The reference image includes at least one target area. The storage device may also be configured to store at least one guidance image of a region of a subject having a guidance image coordinate space. The at least one guidance image may be acquired from a different imaging modality than the reference image. A registration device may be configured to register the reference image including the at least one target area to the at least one guidance image in the guidance image coordinate space. The registration device may also be configured to register a mapped guidance image which includes the at least one guidance image, the at least one target area, and at least one biopsy location indicating a location that an interventional procedure was executed, to the reference image in the reference image coordinate space. An image generation device may be configured to generate on a display device the mapped guidance image based on the registration of the reference image and the guidance image in the guidance image coordinate space. The image generation device may also be configured to generate on a display device a planning image which includes the reference image and the at least one target area and at least one biopsy location based on the registration of the mapped guidance image and the reference image in the reference image coordinate space.

In another embodiment, a system for planning and performing a repeat interventional procedure includes a workstation. The workstation includes one or more processors, memory and an interface. The memory further includes a storage device that may be configured to store a reference image of a region of a subject having a reference image coordinate space. The reference image includes at least one target area. The storage device may also be configured to store at least one guidance image of a region of a subject having a guidance image coordinate space. The at least one guidance image may be acquired from a different imaging modality than the reference image. A registration module may be configured to register the reference image including the at least one target area to the at least one guidance image in the guidance image coordinate space. The registration module may also be configured to register a mapped guidance image including the at least one guidance image, the at least one target area, and at least one biopsy location indicating a location that an interventional procedure was executed, to the reference image in the reference image coordinate space. An image generation module may be configured to generate on a display device the mapped guidance image based on the registration of the reference image and the guidance image in the guidance image coordinate space. The image generation module may also be configured to generate on a display device a planning image which includes the reference image and the at least one target area and at least one biopsy location based on the registration of the mapped guidance image and the reference image in the reference image coordinate space.

In another embodiment, a method for planning and performing a repeat interventional procedure includes the steps of retrieving a reference image of a region of a subject. The reference image includes at least one target area. At least one guidance image of the region of the subject may be retrieved. The at least one target area from the reference image may be registered to a coordinate space for the at least one guidance image and at least one mapped guidance image may be generated. A first interventional procedure may be performed and biopsy locations where the procedure was executed may be recorded in the at least one mapped guidance image. The biopsy locations from the mapped guidance images are registered to the reference image in a coordinate space for the reference image and a planning image may be generated.

The method may include the further steps of retrieving a current reference image of a region of a subject having at least one current target area and a prior planning image generated from a prior interventional procedure. The prior planning image may be registered with the current reference image and a mapped current reference image may be generated having at least one current target area, at least one prior target area and at least one prior biopsy location. The at least one current target area, at least one prior target area and at least one prior biopsy location from the mapped current reference image may be registered to at least one guidance image having a guidance image coordinate space and at least one enhanced guidance image may be generated. A current interventional procedure may be performed and biopsy locations are recorded where the current interventional procedure was executed in the at least one enhanced guidance image. The biopsy locations from the at least one enhanced guidance image may be registered to the mapped current reference image in a coordinate space for the current reference image and an enhanced planning image may be generated.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
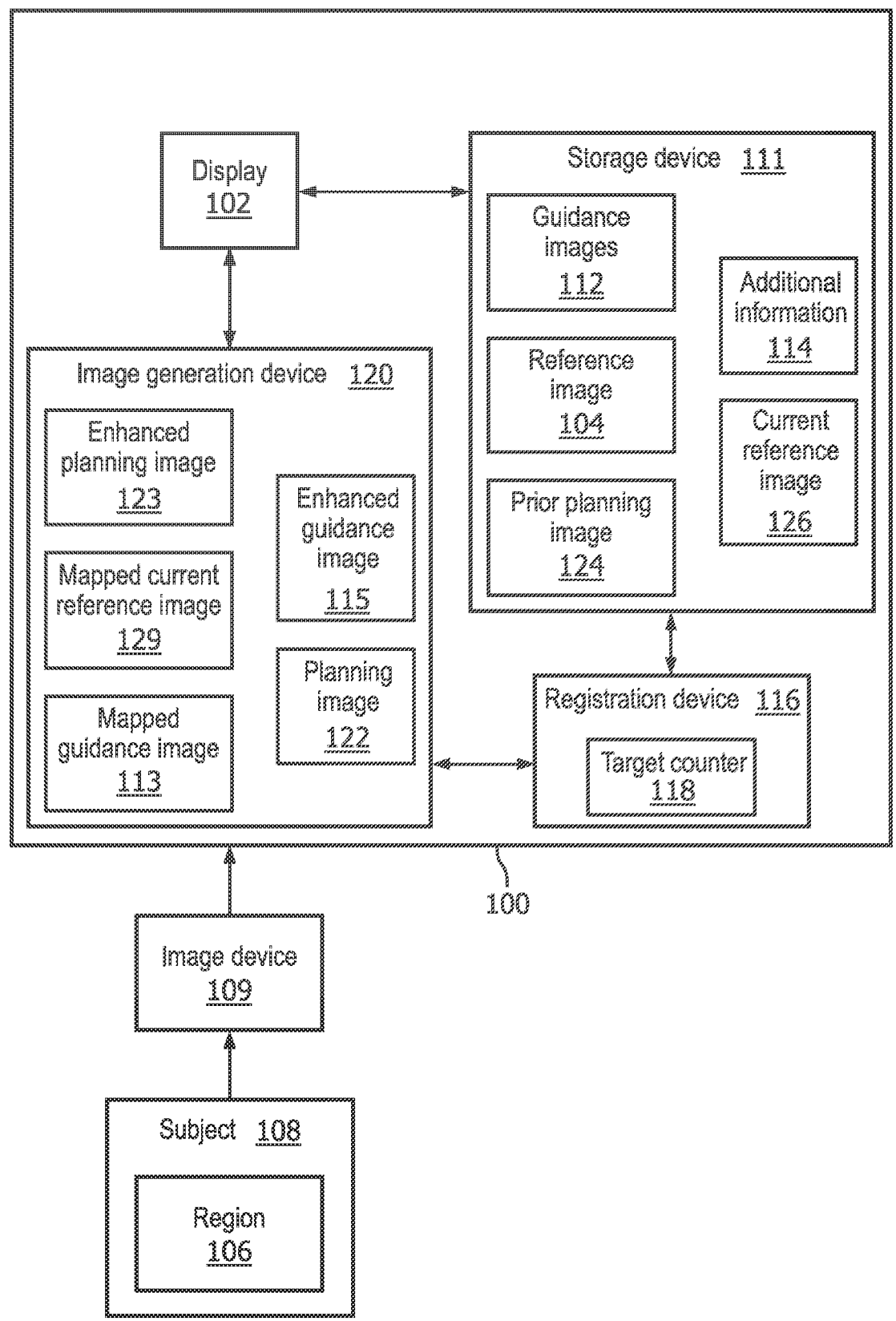
FIG. 1 is a block/flow diagram showing a system for planning and performing a repeat interventional procedure in accordance with one illustrative embodiment.

In accordance with the present principles, a system for planning and performing a repeat interventional procedure is provided which registers current targets in a reference image for a first interventional procedure to a guidance image acquired from a different imaging modality for improved visualization and guidance during the interventional procedure. The system may be configured to record biopsy locations and additional information during the first interventional procedure to the guidance images in the guidance image coordinate space. The system may be configured to register the biopsy locations and map the biopsy locations on the reference image to provide a planning image for use in a subsequent interventional procedure on the patient.

The system may also be configured to register prior biopsy locations, prior target locations and associated additional information from a prior planning image to a current reference image to provide a mapped current reference image for use in a current interventional procedure. The system may be configured to register the current reference image to a guidance image to provide an enhanced guidance image which includes the current targets and the prior targets, prior biopsy locations and additional information from the prior interventional procedure. The system may be further configured to record biopsy locations and additional information during the current interventional procedure to the enhanced guidance images in the guidance image coordinate space. The system may be configured to register the biopsy locations for the current interventional procedure and map the biopsy locations on the mapped current reference image to provide an enhanced planning image for use in subsequent interventional procedures.

The system may employ two different imaging modalities at the time of performing an interventional procedure and may provide a registration therebetween to permit information from prior interventional procedures to be mapped onto the current images for improved planning and performance of a current interventional procedure. The system permits the user to track specific tissue areas over repeat interventional procedures.

It should be understood that the present invention will be described in terms of medical systems. However, the teachings of the present invention are much broader and in some embodiments, the present principles are employed in quantitatively evaluating complex biological or mechanical systems. Furthermore, the present principles are applicable to internal evaluation procedures of biological systems in all areas of the body such as the lungs, liver, brain, uterus, gastro-intestinal tract, excretory organs, blood vessels, and any other solid organ tissue, tumor tissue and homogenously or heterogeneously enhancing structures of the body. The elements depicted in the Figures. may be implemented in various combinations of hardware and software and provide functions which may be combined in a single element or multiple elements.

The functions of the various elements shown in the Figures. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Similarly, it will be appreciated that various processes may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

In accordance with the present principles, a system for planning and performing a repeat interventional procedure is provided. Referring now to the drawings in which like numerals represent the same or similar elements and initially to FIG. 1, a system 100 includes a storage device 111 configured to store a reference image 104 of a region 106 of a subject 108. The reference image 104 may include an MRI image, computed tomography ("CT") image, a positron emission tomography ("PET") image, ultrasound image or an image from other imaging modalities known in the art. In a preferred embodiment, the reference image 104 is an MRI image. An MRI image provides a high resolution, non-realtime image with a relatively large field of view, which is advantageous for image registration and procedure planning. The reference image 104 includes a reference image coordinate space.

The reference image 104 includes at least one target area for a planned interventional procedure. For example, in one illustrative embodiment, the interventional procedure is a biopsy, such as a prostate biopsy. In this embodiment, the target areas would preferably be a region 106 of the subject's prostate where there is an increased suspicion of cancerous tissue. The system 100 may be configured to show the reference image 104 on a display 102. The target areas may be identified by point locations in the reference image 104 or 2D or 3D contours in the reference image indicating the location and shape/size of the targets.

The storage device 111 may also be configured to store at least one guidance image 112 of the region 106 of the subject 108. For example, in the embodiment where the interventional procedure is a prostate biopsy, the guidance images 112 may be images of regions of the subject's prostate. The guidance images 112 are preferably a different imaging modality than the reference image 104. The guidance images 112 are preferably real-time images that are lower resolution and are acquired at a relatively low cost which is advantageous for live image guidance. In one embodiment, the guidance images are ultrasound images. Alternatives such as magnetic particle imaging may be available instead or in addition. The guidance images 112 include a guidance image coordinate space.

The system 100 further includes a registration device 116 that may be configured to spatially register each target area in the reference image 104 to each guidance image 112 in the guidance image coordinate space. In one embodiment, the registration device 116 may be configured to perform an elastic registration transformation. The registration device 116 may be configured to perform the transformation utilizing mutual information as a similarity metric and B-splines as an elastic interpolator, and/or Nelder & Mead's "Downhill Simplex" algorithm for iterative modification of the transformation parameters until the similarity metric is maximized. After the transformation is performed by the registration device 116, the registration device may be configured to apply the transformation to the coordinates of the target areas in the reference image 104 which transforms their location in the reference image to a corresponding anatomical location in the guidance images 112 in the coordinate space of the guidance images. As will be described, the registration device may be configured to perform numerous elastic registration transformations between images in a reference image coordinate space and images in a guidance image coordinate space. The registration device 116 may also include a spatial tracking device, preferably an electromagnetic tracking device, to help register the reference image 104 to the guidance images 112. This tracking may be similar to that employed in the Philips Invivo UroNav™ product.

An image generation device 120 may be configured to generate a mapped guidance image 113 on the display 102 based on the registration. The mapped guidance image 113 may include the guidance image 112 and the mapped target areas from the reference image 104. The target areas may be identified in the mapped guidance images 113 by point locations or by 2D or 3D contours in the guidance images. The mapped guidance images 113 produced by the system permits a practitioner to perform a guided interventional procedure, such as a prostate biopsy, in which the guidance images have the target areas mapped thereon to permit clear visualization of the target areas during performance of the procedure.

The system 100 may be configured to record the locations where the actual biopsies are executed during the interventional procedure in the mapped guidance images 113 in the guidance image coordinates. In other embodiments, the system may be configured to record the locations of the actual biopsies in the guidance images 112. Since targets are often biopsied more than once, the number of biopsy locations may be greater than the number of target areas.

The system 100 may be further configured to record additional information 114 related to the reference image 104 or the guidance images 112 and the associated interventional procedure that is performed in the storage device 111. The additional information 114 preferably pertains to, and is correlated to, the target areas and biopsy locations in the mapped guidance images 113 or the target areas in the reference image 104. The additional information 114 may include information related to the level of the suspicion of cancer for a target area, such as a prostate imaging reporting and data system ("PIRADS") rating. The additional information 114 may further include information concerning the histopathological findings in the biopsy cores obtained at the biopsy locations such as the tissue type, an indication of whether the tissue is benign or malignant, the type of malignancy, the percentage of cancer in the biopsy core, a Gleason score for the tissue, a summary score based on the histopathological findings, etc. The additional information 114 may also include information concerning the anatomical location of the target areas or biopsy locations The registration device 116 may be further configured to register the biopsy locations from each mapped guidance image 113 to the reference image 104 in the reference image coordinates. In some embodiments, the registration device 116 may utilize the transformation between the reference image 104 and the guidance images 112 already obtained in order to perform an elastic registration transformation between the biopsy locations in the mapped guidance image to the reference image coordinate space. In one embodiment, the registration device 116 includes a target counter 118 that may be configured to determine the total number of biopsies ($N_{prior}$) recorded in the mapped guidance images 113. The registration device 116 may be configured to retrieve the mapped guidance images 113 and the associated data such as the biopsy locations ($L_n$).

After the registration transformation $T_{guidance\_reference}$ is determined by the registration device 116 on the biopsy locations, the registration device 116 may be configured to apply the transformation to the coordinates of the biopsy locations in the mapped guidance images 113 and any corresponding additional information 114 concerning the biopsy locations. This transforms their location in the mapped guidance image 113 to a corresponding anatomical location in the reference image 104 in the coordinate space of the reference image. In one embodiment, the $T_{guidance\_reference}$ transformation may also be applied to the imaging data of the guidance image 112 so that the guidance image may be mapped onto the coordinate space of the reference image 104 for retrieval during planning and performance of a subsequent interventional procedure. The registration device 116 may be configured to perform the registration for each of the mapped guidance images 113.

An image generation device 120 may be configured to generate a planning image 122 on the display 102. The planning image 122 includes the reference image 104 which contains the planned targets and the mapped actual biopsy locations from the mapped guidance images 113. The image generation device 120 may also be configured to generate images of any additional information 114 on the planning image 122. The image generation device 120 may also generate one or more of the guidance images 112 in combination with the planning image 122. The system 100 may be configured to store the planning image 122 in the storage device 111.

In a preferred embodiment, the system may be configured to store one or more prior planning images 124 generated during an earlier interventional procedure in the storage device 111 for use with a current interventional procedure. The system may be configured to store a current reference image 126 which is acquired at a later time than the interventional procedure performed in the prior planning image 124. The current reference image 126 includes at least one current target area for the current interventional procedure to be performed on the same region of the subject as the associated procedure in the prior planning image 124. In one embodiment, the current reference image 126 may be an MRI image or another high resolution imaging modality, as previously described. The current target areas may be identified by point locations in the current reference image 126 or 2D or 3D contours in the current reference image indicating the location and shape/size of the target.

The registration device 116 may be configured to register the biopsy locations in the prior planning image 124 to the current reference image 126 via a registration, as previously described. The image generation device 120 may be configured to generate a mapped current reference image 129 which includes the current reference image 126 and the mapped biopsy locations, targets and additional information 114 from the prior planning image 124.

The registration device 116 may be further configured to register the current target areas, prior target areas, prior biopsy locations and additional information in the mapped current reference image 129 to guidance images 112 stored in the storage device 111 for the current interventional procedure. The image generation device 120 may be configured to generate enhanced guidance images 115 on the display 102 based on this registration. The enhanced guidance images 115 includes the guidance images and the mapped current targets and prior biopsy locations, prior targets and additional information from the mapped current reference image 129 in the guidance image coordinate space.

The enhanced guidance images 115 produced by the system permits a practitioner to perform a guided interventional procedure, such as a prostate biopsy, wherein the target areas and the prior biopsies and prior target areas are clearly visualized in the guidance images. The enhanced guidance images 115 may also include additional information 114 related to the prior biopsies or the current targets.

The system 100 may be configured to record the locations where the actual biopsies are executed during the current interventional procedure in the enhanced guidance images 115 in the guidance image coordinates. The system 100 may also be configured to record additional information 114 related to the current interventional procedure and the associated biopsy locations.

The registration device 116 may be further configured to register the biopsy locations from the current interventional procedure in the enhanced guidance images 115 to the mapped current reference image 129 in the current reference image coordinates. The image generation device 120 may also be configured to generate an enhanced planning image 123 which includes the mapped current reference image 129 and the mapped actual biopsy locations from the enhanced guidance images 115. The system 100 may be configured to store the enhanced planning image 123 in the storage device 111 for use as a prior planning image in future repeat interventional procedures on the patient. The storage device 111 may also be configured to store any image generated by the image generation device 120 for use in future interventional procedures. The system may be configured to show any of the images stored in the storage device 111 or generated by the image generation device 120 on the display 102. While the systems are generally described in discrete parts in FIG. 1, the systems and their components may be incorporated into a single system.

In one embodiment, the image generation device 120 may be configured to utilize different visual markers to indicate the additional information 114 in the images that are generated, such as different colors or symbols to indicate the type or severity of the histopathological findings. The image generation device 120 may also be configured to use different colors or symbols to indicate the prior biopsy procedure during which the prior biopsy locations were obtained. For example, each target area or biopsy location in the generated images may have a distinct color to indicate the time period of the target or biopsy location.

Figure 2:
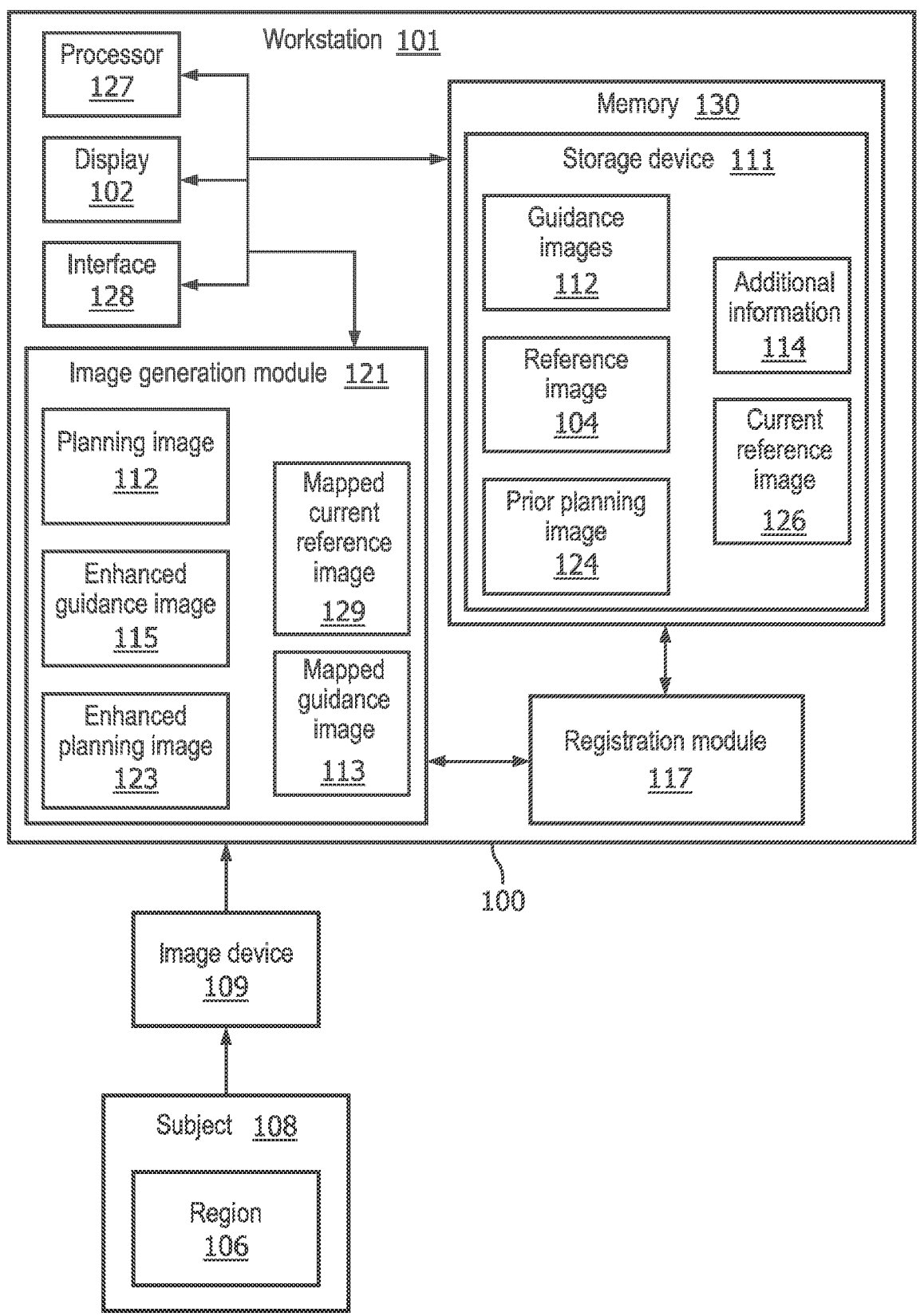
FIG. 2 is a block/flow diagram showing a system for planning and performing a repeat interventional procedure in accordance with a second illustrative embodiment.

As shown in FIG. 2, in one embodiment, the system 100 may include a workstation 101 from which the procedure is supervised and/or managed. The workstation 101 preferably includes one or more processors 127 and memory 130 for storing programs and applications. In one embodiment, the storage device 111 may be integrated within the memory 130 of the system. The display 102 permits a user to view images and interact with the workstation 101. In one embodiment, the workstation 101 may include a separate display than the display 102 which shows the reference, guidance and planning images. The system 100 may further include an interface 128 which may feature a keyboard, mouse, a joystick, a haptic device, or any other peripheral or control to permit user feedback from and interaction with the workstation 101.

The workstation 101 may also include an integrated registration module 117 which may be configured to register the images and the target areas, biopsy locations and/or additional information 114 associated therewith to different coordinate spaces and provide the same functionality as the registration device 116 previously described in the embodiment shown in FIG. 1.

The workstation 101 may also include an integrated image generation module 121 which may be configured to generate images and provide the same functionality as the image generation device 120 previously described in the embodiment shown in FIG. 1.

The system 100 described in FIGS. 1-2 provides the user with images which includes the current target areas as well as the previous target locations and biopsy locations. The system 100 may also provide the user with the additional information 114 concerning the prior interventional procedures or the current procedure. The system provides the user with an improved visualization of images of the region and the information from the prior interventional procedures in order to permit the user to plan and perform a repeat, targeted interventional procedure.

The system 100 shown in FIGS. 1-2 may be configured to allow the user to interact with the visualization such as enabling the user to choose which images, targets and prior biopsy locations that the image generation device 120 or image generation module 121 displays in the images. The system 100 may also be configured to allow the user to input further information associated with each of the targets or biopsy locations. For example, the system may be configured to allow the user to input the further information into the workstation 101 via the interface 128.

The system 100 may also be configured to receive information from the user during the performance of the interventional procedure and record the information in the storage device 111. For example, the information inputted by the user during the interventional procedure may include new biopsy locations, targets and/or associated pathology results. The system 100 may also receive new images of the region of the subject acquired by an imaging device 109, such as an MRI, during the interventional procedure. The system 100 may be configured to associate the information inputted during the procedure with the targets or biopsy locations in the images. The system permits the user to perform the interventional procedure while viewing the various guidance images and adjust the planned procedure, as necessary. The reference and planning images may be used to plan the current interventional procedure and subsequent interventional procedures.

Figure 3:
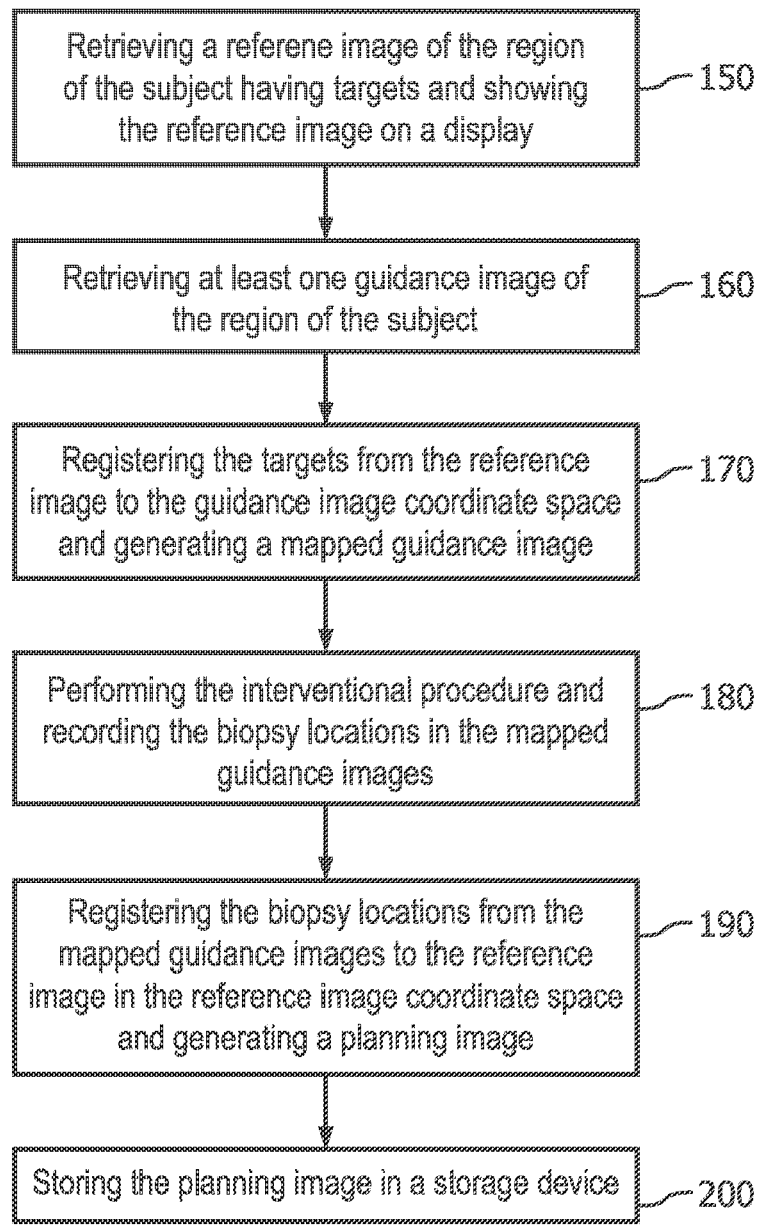
FIG. 3 is a flow diagram showing a method for planning and performing a repeat interventional procedure in accordance with one illustrative embodiment.

Referring to FIG. 3, a method 140 for planning and performing an interventional procedure is illustratively shown in accordance with the present principles. In block 150, a reference image 104 having at least one target area for an interventional procedure may be retrieved and shown on a display. In block 160, at least one guidance image 112 of the region of the subject may be retrieved. The at least one guidance image 112 may be a different imaging modality than the reference image.

In block 170, the at least one target area from the reference image 104 may be registered to the coordinate space of the guidance image and a mapped guidance image 113 may be generated which includes the guidance image and the target area in the guidance image coordinate space. In block 180, the interventional procedure may be performed and the biopsy locations where the actual biopsies are executed are recorded in the mapped guidance images 113 in the guidance image coordinates.

In block 190, the biopsy locations from each mapped guidance image 113 may be registered to the reference image 104 in the reference image coordinates and a planning image 122 may be generated which includes the reference image 104, the planned targets and the mapped actual biopsy locations from the mapped guidance images 113. Additional information 114 related to the mapped actual biopsy locations, such as the diagnostic pathology results, may also be registered during this step 190. In block 200, the planning image 122 may be stored in a storage device 111.

Figure 4:
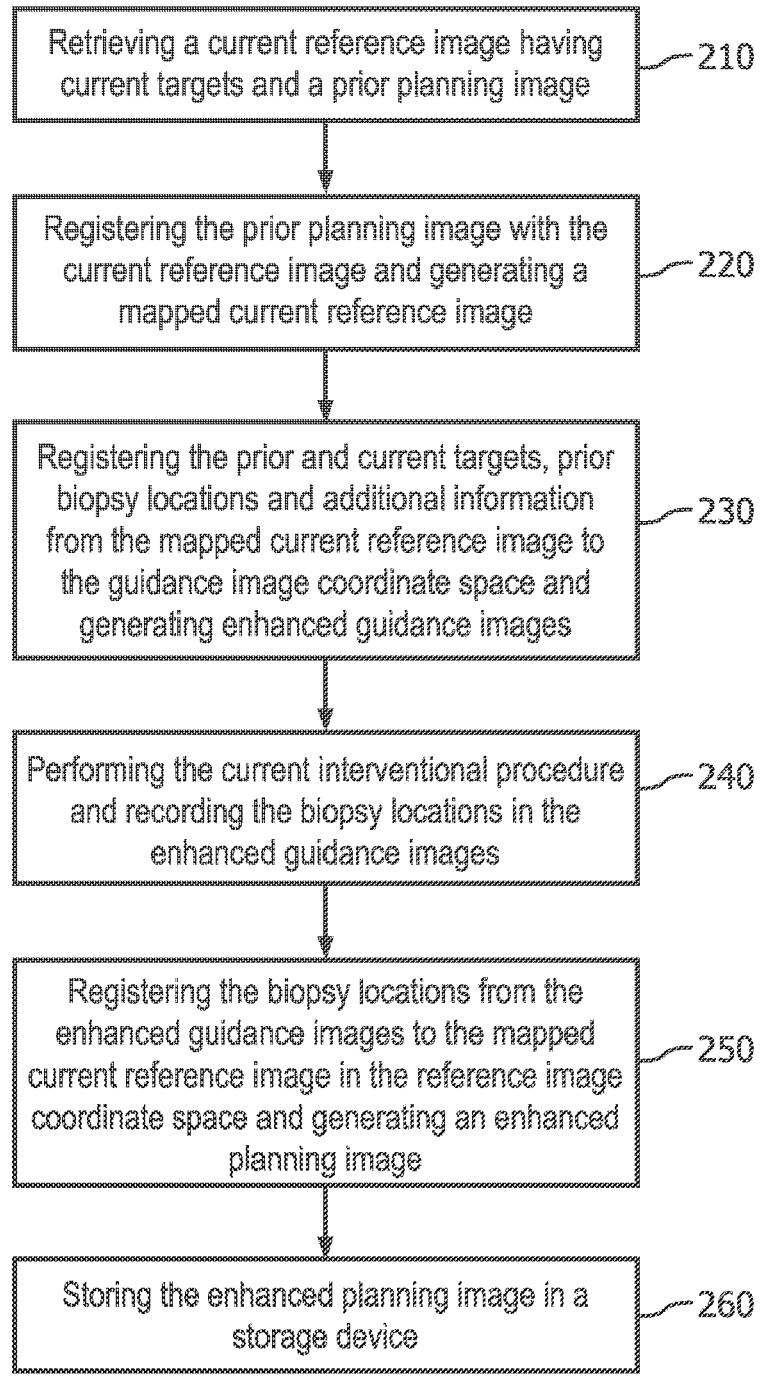
FIG. 4 is a flow diagram showing a method for planning and performing a repeat interventional procedure in accordance with a second illustrative embodiment.

As shown in FIG. 4, in a preferred embodiment, the method further includes the step in block 210 of obtaining a prior planning image 124 generated during a prior interventional procedure as well as a current reference image 126 based on a recent reference image acquired after the prior interventional procedure. The current reference image 126 includes at least one current target area. In block 220, the prior planning image 124 may be registered with the current reference image 126 and a mapped current reference image 129 may be generated which includes the current reference image, the current targets and the mapped prior biopsy locations, prior target locations and associated additional information from the prior planning image 124.

In block 230, the target areas, biopsy locations and associated additional information from the mapped current reference image 129 may be registered to at least one guidance image 112 and enhanced guidance images 115 may be generated on a display 102 based on the registrations. The enhanced guidance images 115 include guidance images, the mapped current targets, the prior biopsy locations, prior targets and associated additional information 114 from the mapped current reference image 129 in the guidance image coordinate space. In block 240, a current interventional procedure may be performed and the biopsy locations where the actual biopsies are executed may be recorded in the enhanced guidance images 115 in the guidance image coordinates.

In block 250, the biopsy locations for the current interventional procedure may be registered with the mapped current reference image 129 and an enhanced planning image 123 may be generated which includes the mapped current reference image, the mapped actual biopsy locations from the current interventional procedure and any additional information from the current interventional procedure. In block 260, the enhanced planning image 123 may be stored in a storage device and may be used in subsequent interventional procedures on the subject.

This method for planning and performing a repeat interventional procedure permits the user to track specific portions of the region over repeat procedures and to visualize the locations, targets and results of the prior interventional procedures on the recent reference image. The method may use two different imaging modalities during each interventional procedure and may performs a registration therebetween. This method permits the user to plan the procedure in a targeted manner and guides the user during the performance of the interventional procedure.

It is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for the system and method for planning and performing a repeat interventional procedure in a subject (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for planning and performing a repeat interventional procedure, comprising:
a computer-readable memory configured to store:
a reference image of a region of a subject having a reference image coordinate space, the reference image including at least one target area, markers indicative of a plurality of prior biopsy locations and diagnostic pathology results for each of the prior biopsy locations;
a series of real-time guidance images of a region of a subject having a guidance image coordinate space, wherein said series of guidance images are acquired from a different imaging modality than the reference image;
one or more computer processors configured to:
register the reference image including the at least one target area and the markers to the series of real-time guidance images in the guidance image coordinate space to generate a series of real-time enhanced guidance images comprising the series of real-time guidance images, the at least one target area, and the prior biopsy locations and the diagnostic pathology results;
register the series of real-time enhanced guidance images to the reference image in the reference image coordinate space;
control a display device to display the series of real-time enhanced guidance images in the guidance image coordinate space, wherein a clinician performing the interventional procedure can view the series of real-time guidance images, the at least one target area, the prior biopsy locations and the indicators of pathology results on the display device in real-time; and
control the display device to display a planning image which includes the reference image, the at least one target area and the plurality of biopsy locations based on the registration of the series of enhanced guidance images and the reference image in the reference image coordinate space.

2. The system as recited in claim 1, wherein:
the computer memory is further configured to store:
a prior planning image generated from an earlier interventional procedure, said prior planning image including at least one prior target area, at least one prior biopsy locations and an indicator of diagnostic pathology for each biopsy location;
a current reference image including at least one current target area for planning a current interventional procedure;
the one or more computer processors are configured to:
register the prior planning image to an image coordinate space of the current reference image;
register a series of real-time enhanced guidance images each including the at least one current target area, the prior biopsy locations and at least one current biopsy location indicating a location at which the current interventional procedure was executed, to the current reference image in the reference image coordinate space;
control the display device to display a mapped current reference image comprising the current reference image and the at least one prior target area and at least one prior biopsy location from the prior planning image;
control the display device to display the series of real-time enhanced guidance images based on registration of the series of real-time guidance images and the mapped current reference image; and
control the display device to display an enhanced planning image, said enhanced planning image including the mapped current reference image and the at least one current biopsy location from the enhanced guidance image based on a registration by the registration device.

3. The system as recited in claim 1, wherein the diagnostic pathology results include information related to a level of suspicion of cancer at each of the prior biopsy locations, histopathological findings of biopsy cores obtained at each of the prior biopsy locations, anatomical location information of the at least one target area or the prior biopsy locations and how long ago the biopsies were performed at each of the prior biopsy locations.

4. The system as recited in claim 3, wherein the image device is configured to generate images indicative of at least one of anatomical location information of the at least one target area and the prior biopsy locations, and how long ago the biopsy was performed at each location.

5. The system as recited in claim 1, wherein the system is configured to display the reference image and/or the series of real-time guidance images on the display device.

6. The system as recited in claim 1, wherein the system is configured to record and store information received from a user during performance of the interventional procedure.

7. The system as recited in claim 6, wherein the system is configured to record and store images from an imaging device during performance of the interventional procedure.

8. The system as recited in claim 1, wherein the reference image is a magnetic resonance imaging image and the series of guidance images are ultrasound images.

9. The system as recited in claim 1, wherein the interventional procedure comprises a prostate biopsy.

10. A system for planning and performing a repeat interventional procedure, comprising:
a workstation including one or more processors, a computer memory, an interface, and a display device,
wherein said computer memory is configured to store:
a reference image of a region of a subject in a reference image coordinate space, the reference image including at least one target area and markers at a plurality of prior intervention locations;

a series of real-time guidance images of the region of a subject in a guidance image coordinate space, wherein said series of real-time guidance images is acquired from a different imaging modality than the reference image;
wherein the one or more processors are configured to:
  register the reference image including the at least one target area and the markers to the series of real-time guidance images to generate a series of enhanced real-time images in the guidance image coordinate space;
  register a series of current guidance images including the at least one target area, and markers indicating the locations at which the prior interventional procedures were executed, to the reference image in the reference image coordinate space; and
wherein the display device is configured to display:
  the series of enhanced real-time guidance images in the guidance image coordinate space, wherein the enhanced real-time guidance images each includes markers indicative of current interventional procedure interventional locations; and
  a planning image which includes the reference image and the target area and the prior interventional procedure locations based on the registration of the enhanced real-time guidance images and the reference image in the reference image coordinate space.

11. The system as recited in claim 10, wherein:
the computer memory is further configured to store:
  a prior planning image comprising a planning image generated from an earlier interventional procedure, said prior planning image including at least one prior target area and prior interventional procedure locations and information concerning each prior interventional procedure location; and
  a current reference image including at least one current target area for a current interventional procedure;
the one or more processors are configured to register:
  the prior planning image to an image coordinate space of the current reference image; and
  a series of enhanced current real-time guidance images including the at least one current target area, the prior interventional procedure locations, at least one current interventional procedure location indicating a location at which the current interventional procedure was executed and information concerning each current interventional procedure location, to the current reference image in the reference image coordinate space;
the display device is configured to display:
  a mapped current reference image mapped to guidance image coordinate space and comprising the current reference image, the at least one prior target area, the prior interventional procedure locations and the information concerning each prior interventional procedure location from the prior planning image;
  the enhanced real-time current guidance images and the mapped current reference image; and
  an enhanced planning image, said enhanced planning image including the current reference image and the at least one current interventional procedure location from the enhanced guidance images.

12. The system as recited in claim 10, wherein the information concerning each prior interventional procedure location includes information related to a level of suspicion of cancer for the corresponding interventional procedure location, histopathological findings of biopsy cores obtained at the prior biopsy locations or anatomical location information of the interventional procedure locations.

13. The system as recited in claim 10, wherein the computer memory is configured to record and store information received from the interface during performance of the interventional procedure and/or images from an imaging device acquired during performance of the interventional procedure.

14. The system as recited in claim 10, wherein the display is further configured to display each marker with a color or an icon to indicate the histopathological findings of the biopsy core obtained at a corresponding prior biopsy location.

15. A method for planning and performing a repeat interventional procedure, comprising:
  retrieving a reference image of a region of a subject, said reference image having at least one target area and markers at a plurality of prior biopsy locations;
  retrieving a series of real-time guidance images of the region of the subject, the series of real-time guidance images being acquired from a different imaging modality than the reference image;
  registering the at least one target area and the markers from the reference image to a coordinate space for the series of real-time guidance images and generating a series of real-time mapped guidance images, wherein the series of real-time mapped guidance images each include the markers;
  performing a first interventional procedure and recording each biopsy location where the procedure was executed in the spaced real-time mapped guidance images;
  registering the biopsy locations from the series of real-time mapped guidance images to the reference image in a coordinate space for the reference image;
  retrieving information indicative of at least one of a level of suspicion of cancer and histopathological findings of biopsy cores obtained at corresponding biopsy locations;
  generating a planning image based on the reference image and the retrieved information; and
  generating a visual display of the planning image with the markers visually encoded to indicate at least one of the level of suspicion of cancer and the histopathological findings at the corresponding biopsy locations.

16. The method of claim 15, comprising the further steps of:
  retrieving a current reference image of a region of a subject having at least one current target area, the markers, and the planning image generated from a prior interventional procedure;
  registering the planning image with the current reference image and generating a current reference image having at least one current target area, at least one prior target area, and the markers at the prior biopsy locations;
  registering the at least one current target area, prior target area and the markers at the prior biopsy locations from the mapped current reference image to each of a series of current real-time guidance images in a guidance image coordinate space to generate a series of real-time enhanced guidance images, each including at least the at least one current target area and the markers visually encoded in accordance with the retrieved information;
  performing a current interventional procedure and recording current biopsy locations, while displaying the series of current guidance images as the current interventional procedure is executed;

registering the current biopsy locations from the series of enhanced guidance images to the current reference image in a coordinate space for the current reference image; and retrieving information indicative of at least one of a level of suspicion of cancer and histopathological findings of biopsy cores obtained at the current biopsy locations;

generating an enhanced planning image.

17. The method of claim 16, comprising the further step of recording and storing additional information received from a user during execution of the current interventional procedure and/or images from an imaging device acquired during the execution of the current interventional procedure.

18. The method of claim 15, comprising the further step of retrieving additional information concerning the the series of mapped real-time guidance images, said additional information comprising information related to at least one of the level of suspicion of cancer for the at least one target area and the histopathological findings of biopsy cores obtained at the corresponding biopsy locations and displaying the series of mapped real-time guidance images with the visually encoded markers.

19. The method of claim 15, wherein the reference images are magnetic resonance images and the series of real-time guidance images are ultrasound images.

* * * * *